United States Patent [19]
Mehl, Sr. et al.

[11] Patent Number: 5,906,610
[45] Date of Patent: May 25, 1999

[54] MELANIN ENHANCED HAIR COLORATION

[76] Inventors: Thomas L. Mehl, Sr., P.O. Box 1019, Newberry, Fla. 32669; Nardo Zaias, 5189 Alton Rd., Miami Beach, Fla. 33140

[21] Appl. No.: 08/989,452

[22] Filed: Dec. 12, 1997

Related U.S. Application Data

[62] Division of application No. 08/634,569, Apr. 18, 1996, Pat. No. 5,766,214.

[51] Int. Cl.$^6$ ..................................................... A61B 17/36
[52] U.S. Cl. ............................ 606/9; 8/405; 8/103; 8/444
[58] Field of Search ............................... 606/2–19; 8/103, 8/405–435, 444, 115.52; 128/898

[56] References Cited

U.S. PATENT DOCUMENTS

| | | | |
|---|---|---|---|
| 4,792,341 | 12/1988 | Kozikowski et al. | 8/103 |
| 5,059,192 | 10/1991 | Zaias | 606/9 |
| 5,226,907 | 7/1993 | Tankovich | 606/9 |
| 5,425,728 | 6/1995 | Tankovich | 606/9 |
| 5,472,456 | 12/1995 | Larsky et al. | 8/405 |

FOREIGN PATENT DOCUMENTS

WO95/15725  6/1995  WIPO.

*Primary Examiner*—Beverly M. Flanagan
*Assistant Examiner*—Rosiland Kearney
*Attorney, Agent, or Firm*—Sven W Hanson

[57] ABSTRACT

A method of altering skin tissues by application of light energy. Hair coloring is altered by introduction of melanin to the hair and hair follicle. Delivery of melanin is enhance by encapsulation in a liposome. Liposomes are specifically selected for the ability to bind to the tissues of the epidermis. Light energy is applied to release the melanin and assist binding to the targeted tissues. Light energy is preferably provided by one of several laser light sources. The light energy is matched to the absorption of the melanin to reduce absorption and damage to surrounding untargeted skin tissues.

3 Claims, No Drawings

MELANIN ENHANCED HAIR COLORATION

RELATED APPLICATIONS

This application is a divisional application of Ser. No. 08/634,569; filed Apr. 18, 1996, now U.S. Pat. No. 5,766,214 which is incorporated herein by reference.

BACKGROUND OF THE INVENTION

The present invention pertains to methods of altering human tissues by application of light energy. Specifically the present invention is a method of dyeing or coloring hair by introducing melanin to the hair follicle by liposome delivery and light activation.

Light energy is used in a variety of methods of tissue treatment including methods of depilation and skin exfoliation. Until now, effective use of light energy to effect a coloration change in hair has not been available.

OBJECTS AND SUMMARY OF THE INVENTION

It is an object of the present invention to provide a method of inducing a coloring change or enhancement to hair by introducing melanin.

It is a further object of the invention to provide a method of delivering a coloring agent to human hair in a highly efficient manner by liposome encapsulation and delivery.

It is another object of the invention to provide a method of delivering melanin to the hair as a coloring agent by encapsulating the melanin in a liposome and subsequently accelerating release of the melanin by application of light energy.

The present invention encompasses methods for adding color to hair. This is accomplished by preferentially depositing additional quantities of melanin at the hair shaft and follicle site or its proximity. This preferential deposition is effected by encapsulating a melanin compound in a liposome specifically selected and formed to bind to specific sites at the epidermis in the proximity of the hair follicle and hair shaft. In use, such a liposome or liposome carrying medium is applied topically to the skin and hair. After the liposome has carried the melanin to the hair, laser energy of a frequency which is readily absorbed by the melanin is directed at the skin. The laser energy is absorbed by the encapsulated melanin releasing it from the liposome and allowing absorption by, or affixation to, the hair follicle and shaft. The present invention employs a variety of light energy sources, both coherent and incoherent, including such lasers as ruby red and Nd-YAG, alexandrite, and diode lasers, or any other light source providing an effective frequency and intensity. To effect energy absorption by melanin, the light energy should be in the wavelength range of 400 to 1500 nm. The inventive methods are best understood with respect to the following detailed descriptions which are provided for illustration.

DESCRIPTION OF THE PREFERRED EMBODIMENTS

While the below discussion focuses on depilation methods, the same concepts of preferential absorption are applicable to methods of hair coloring where the light energy is used to release and affix a coloring agent. Light energy levels for these purposes are reduced from those effecting depilation.

In using high energy light sources such as lasers on mammalian skin, it is preferable to use the minimal amount of treatment required to achieve the objective. As with chemical epidermal treatments, overdosage can cause unwanted scarring or damage. A ruby laser is preferred to produce the desired effect of depilation and eliminate hair regrowth.

However, to reduce the required exposure in using any laser, as well as other light sources, and thereby avoid producing unwanted side-effects, such as scarring, the following method of introducing additional melanin to the follicle region has been developed. In addition to reducing the required light energy exposure for effective hair removal, by increasing the relative absorption of the target, this method allows the use of laser light of wavelengths that would be otherwise excessively damaging to the surrounding skin. Prior to discussing a liposome delivery process for addition of melanin, the process of laser photothermolysis for depilation will first be detailed.

Using the process of selective photothermolysis, a laser wavelength is matched with the absorption spectrum of the melanin found at the base of the hair follicle. Melanin is a pigment which is concentrated at the base of the follicle and which has an absorption spectrum that is highest in the ultraviolet range and gradually diminishes toward the infrared. The depth of penetration of light is dependent on its wavelength and duration of pulse and longer wavelengths are required to damage the hair follicle deep in the dermis as well as germative tissue in the bulge region.

Therefore, the depth of penetration can be selected through the selection of an appropriate wavelength, desired pulse duration and the damage at a particular depth is controlled by the energy applied. Of course, as higher energy levels are used, the depth of penetration will be increased through the generation and accumulation of heat through absorption. A careful balance of the laser parameters leads to destruction of the hair follicle without permanently destroying normal adjacent epidermal and dermal structures.

In a first step, the hair shaft is cut down to the near the surface of the skin. The shaft extends down to the follicle which at the anagen stage of the hair cycle joins the papilla. It is generally accepted that destruction of the papilla is necessary to prevent hair regrowth. After growing for about three years in the anagen stage, the hair shaft enters the catagen stage wherein the papilla separates from the base of the follicle. The catagen stage lasts only a few weeks. In the telogen stage of the hair cycle, the papilla completely separates from the follicle and forms a new secondary hair germ which will repeat the cycle. The telogen stage lasts about three months. In order to assure sufficient injury to the papilla at the telogen stage as well as the papilla at the anagen stage, use of a light source with sufficient energy and depth of penetration is usually necessary to achieve sufficient melansomal destruction.

Cutting of the hair shaft down to the skin provides two important functions of the treatment process. First, the tip of the hair shaft allows the operator to position the light source substantially vertically over the hair follicle opening such that an optimum location for aiming the light energy to strike the papilla is obtained. Second. the reduction of excess hair eliminates additional scattering of the radiant energy contained.

Application of the laser pulse to the follicle and the papilla causes photothermolysis which provides melanosomal disruption, including vaporization of the melanin in the follicle and papilla as well as vacuolation, edema, gas bubbles and protein denaturation. When the radiation absorbed is of sufficient energy level, these effects seriously injure the hair follicle and papilla, thereby damaging the hair germative cells which causes hair regrowth.

The hair follicle may extend into the reticular dermis up to 3 millimeters (mm) from the skin surface. In order to achieve the depth of penetration required to destroy the hair follicle, it has been found that a wavelength of about 694 nm, which is produced by the ruby red laser, is preferred. The ruby red laser tends to produce less severe dermal injury.

Where the hair follicle has not been enhanced by addition of melanin, or other enhancing compound, the degree of follicular injury is solely dependent on the radiant exposure dose to the existing melanin. Without melanin enhancement, follicular damage is first observed at as low as 0.4 J/cm$^2$. At such a low dose, the hair may fall out of the skin. However, normal regrowth will soon occur. Scarring has been found to occur at about 10 J/cm$^2$. While an exposure dose of 8.0 J/cm$^2$ has previously been found to be optimum, with the enhancement of the target follicles with liposome delivered melanin, the required effective doses may be reduced.

The upper limit of exposure dose for laser hair removal is set by collateral damage to the surrounding skin. To improve the effectiveness of applied light energy in causing hair follicle death, the present invention introduces additional melanin to the hair follicle region to enlarge the effective target. In this manner a greater portion of the incident energy is directed to death of the hair follicle and germative cells.

Although the above description has been principally in terms of lasers as the light energy source producing photothermolysis, incoherent light sources can be similarly applied so long as the wavelength and intensity of light produced meets the above requirements. In the same vain, it is possible to control pulsed, continuous wave, and q-switched lasers as well as others to effect photothermolysis of germative cells in this process. An example of such a light source in a therapeutic application is provided in U.S. Pat. No. 5,344,434 to Talmore.

To accomplish the preferential delivery of melanin to the hair follicle a liposome based system has been developed. Liposomes have the combined benefits of providing an encapsulating and carrying means as well as being able to be structured for selective delivery of its contents.

Liposomes provide a non-toxic means for encapsulation and can be further modified to bind to specific sub-populations of cells. Specifically, the liposome membranes according to the present invention can be made to bind to specific sub-populations of the basal cell region in the proximity of the hair follicle thereby increasing efficiency and specificity of melanin delivery. There are currently two theories regarding the optimum target region for thermolysis as a means of preventing hair regrowth. The generally accepted theory is that destruction of cells at the depth of the papilla is required to prevent cells in the telogen stage from forming new hair. The above description of depilation is generally based on this presumption. However, a second theory is that regrowth may be prevented by destruction of cells no deeper than what is known as the "bulge" region of the hair follicle. Liposomes in the present invention can be selected to bind preferentially to cells in either, or both, of the bulge and papilla regions. In this way, laser depilation under either theory may be enhanced by the introduction of melanin into the target region.

Liposomes have also been previously used to encapsulate melanin for introduction into non-pigmented human fibroblast. See "Polyethylene-Glycol-mediated Delivery of Liposome-entrapped Pigments into Fibroblasts: Experimental Pigment Cells as Models for Mutator Phenotypes" by S. Schmitz, T. M. Allen and K. Jimbow in CANCER RESEARCH, 1992, Vol. 52, pp. 6638–6645.

Liposomes are microscopic spherical membrane-enclosed vesicles or sacs made artificially in the laboratory by a variety of methods. The primary requirements according to the present invention are that the liposomes should not be toxic to the living cells and that they should preferentially bind to, or otherwise be constrained to, the hair follicle vicinity. The liposomes according to the present invention may be of various size and may comprise either one or several membrane layers separating the internal and external compartments. An important element in liposome structures is that the liposome be resistant to destruction as it travels from the surface of the skin down to the target region. Liposome structures according to the present invention include small unilamellar vesicles (less than 250 angstroms in diameter), large unilamellar vesicles, and multilamellar vesicles.

The liposomes according to the present invention may be made from natural and synthetic phospholipids, glycolipids and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activities.

The liposomes of the present invention may be prepared by combining a phospholipid component with an aqueous component containing the selected melanin compound under conditions which will result in vesicle formation. The phospholipid concentration must be sufficient to form lamellar structures, and the aqueous component must be generally compatible with the melanin compound to be encapsulated. Methods for combining the phospholipid and the aqueous components so that vesicles will form include: drying the phospholipids onto glass and then dispersing them in the aqueous components; injecting phospholipids dissolved in a vaporizing or non-vaporizing organic solvent into the aqueous component which has previously been heated; and dissolving phospholipids in the aqueous base with detergents and then removing the detergent by dialysis. The liposomes can be produced from the foregoing mixtures either by sonication or by dispersing the mixture through either small bore tubing or through the small orifice of a French Press. The methods for producing the liposomes as set forth in U.S. Pat. No. 5,077,211 to Yarosh are incorporated herein by reference.

It is within the scope of the present invention to use other methods for encapsulating melanin within a liposome. A specific example of producing the liposomes would include the following process. A lipid mixture as set forth above is dissolved in an organic solvent and dried to a thin film in a glass vessel. The selected melanin compound is purified and added to the vessel at high concentrations in an aqueous buffer to rehydrate the lipid. The mixture is then agitated by vortexing and sonicated to form liposomes. The liposome spheres containing the encapsulated melanin compound are then separated from the unincorporated melanin compound by centrifugation or gel filtration.

A similar process for producing liposome encapsulated melanin is provided in the above work by Allen and Jimbow. In that process, liposomes are formed of a egg phosphatidylcholine and cholesterol mixture and then repeatedly extruded through polycarbonate membranes to increase uniformity of size. The unencapsulated melanin was removed by gel filtration. Generally, uniformity of size is not critical in delivery of melanin for the present invention. However, use of smaller liposomes may be advantages due to increased stability. This method in incorporated by reference.

The prepared liposome encapsulated melanin is administered to the hair follicle by topical application to the skin. Administration to humans requires that the liposomes be pyrogen-free and sterile. To eliminate pyrogens, pyrogen-free raw materials, including all chemicals as well as the melanin compounds and water are used to form the liposomes. Sterilization can be performed by filtration of the liposomes through a 0.2 micron filter. An effective concentration of liposomes is then suspended in a buffered polymeric glycol gel carrier for even application to the skin. In general, the gel carrier should not include non-ionic detergents which can disrupt the liposome membranes. Other similar vehicles can also be used to topically administer the liposomes. The concentration of the melanin in the final preparation can vary over a wide range and the desired concentration will depend upon parameters such as the laser light to be applied and the nature of the target skin and hair.

A general discussion of liposomes and liposome technology can be found in a three volume work entitled Liposome Technology edited by G. Gregoriadis, 1993, published by CRC Press, Boca Raton, Fla. The pertinent portions of each of these references are incorporated herein by reference.

Melanin, and melanin compounds, as used herein, refer to the family of compounds which exist naturally as the coloring pigment in mammalian skin and hair.

After the hair follicle region has been enhanced with melanin deposited liposomes, the skin is exposed to high intensity light energy. While the ruby red laser produces a preferred light energy in that it matches well the absorption range of melanin, the enhancement of the hair follicle as a target makes possible use other light frequencies. Diode lasers within the proper frequency can be used with similar effectiveness when configured to provide for sufficient power. Laser light such as produced by lasers other than the ruby red laser is not absorbed as readily by the natural melanin and surrounding skin. The consequence is unacceptable scarring. However, after the hair follicles have been enhanced with melanin by the above process the overall exposure can be reduced sufficiently to reduce or eliminate scarring such that a broad range of light sources can be successful employed in effecting permanent hair loss. As a result the present method may be successfully applied using any light source producing light of a frequency readily absorbed by melanin. The applicable wavelength range is about 400 to 1500 nm. This includes lasers commonly known as the ruby red, Nd-Yag, alexandrite, and diode lasers.

The above methods are extended to processes for the dyeing of hair. This is accomplished by preferentially depositing additional quantities of melanin at the hair shaft and follicle site or its proximity. This preferential deposition is effected by encapsulating a melanin compound in a liposome specifically selected and formed to bind to specific sites at the epidermis in the proximity of the hair follicle and hair shaft. In use, such a liposome or liposome carrying medium is applied topically to the skin and hair. After the liposome has carried the melanin to the hair, laser energy of a frequency which is readily absorbed by the melanin is directed at the skin. The laser energy is absorbed by the encapsulated melanin releasing it from the liposome and allowing absorption by, or affixation to, the hair follicle and shaft. Application of light energy of a intensity and total energy level below that causing photothermolysis is used. While this invention has been described as having a preferred method, it is understood that it is capable of further modifications, uses and/or adaptions and that these and such departures from the present disclosure as have come within known or customary practice in the art fall within the scope of the invention or the limits of the claims appended hereto.

We claim:

1. A method of hair dyeing comprising the steps of:

a. applying liposome encapsulated melanin to the hair, and skin tissue surrounding the hair follicles, b. aligning a light source over said hair and skin tissue, and c. applying to said skin area light energy of sufficient energy and duration to release the encapsulated melanin and effect a darkening of the hair.

2. The method of claim 1, wherein:

said light energy is of a wavelength which is readily absorbed by the melanin.

3. The method of claim 2, further comprising the step of:

selecting a liposome having the property of preferably residing in the proximity of the hair follicle upon application to the skin.

\* \* \* \* \*